United States Patent
Inui et al.

(10) Patent No.: US 6,310,144 B1
(45) Date of Patent: *Oct. 30, 2001

(54) REINFORCED RUBBER ARTICLE, PRODUCTION THEREOF AND RUBBER COMPOSITION SUITABLE THEREFOR

(75) Inventors: Naoki Inui, Yamatokoriyama; Hideo Nagasaki, Osaka; Tetsuo Yamaguchi, Toyonaka, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/459,678

(22) Filed: Jun. 2, 1995

Related U.S. Application Data

(62) Division of application No. 08/193,758, filed on Feb. 3, 1994, now abandoned.

(30) Foreign Application Priority Data

Feb. 3, 1993 (JP) .................................................. 5-016363
Feb. 3, 1993 (JP) .................................................. 5-016364

(51) Int. Cl.$^7$ .......................... B32B 25/02; C08C 19/22; C08K 5/3437
(52) U.S. Cl. .................. 525/332.5; 428/625; 525/332.7; 525/347; 525/375
(58) Field of Search .............................. 428/411.1, 610, 428/625, 677, 295.1, 296.4; 526/259; 525/332.5, 322.6, 332.7, 347, 370, 375

(56) References Cited

U.S. PATENT DOCUMENTS

| | | | |
|---|---|---|---|
| 4,158,000 | 6/1979 | Nagasaki et al. | 260/45.8 NW |
| 4,326,062 | 4/1982 | Kojima et al. | 546/166 |
| 4,929,512 | * 5/1990 | Nishimura et al. | 428/610 |
| 4,947,916 | * 8/1990 | Ishikawa et al. | 152/536 |
| 5,665,799 | * 9/1997 | Inui et al. | 524/87 |

FOREIGN PATENT DOCUMENTS

| | | |
|---|---|---|
| 2398088 | 2/1979 | (FR) . |
| 53-18651 | 2/1978 | (JP) . |
| 57-18745 | 1/1982 | (JP) . |
| 57-85835 | 5/1982 | (JP) . |
| 61-31444 | 2/1986 | (JP) . |

OTHER PUBLICATIONS

Sato, "Antioxidants for Rubber", Feb, 8, 1979, CA#90:188331.*
Ishikawa, "Radial Tires", Jul. 4, 1989, CA#112:8621.*
*Chemical Abstracts*, vol. 58, No. 5, Mar. 11, 1963, Columbus, Ohio, U.S.; L.P. Zalukajevs et al., "The constitution of a dimer of 2,2,4-trimethyl-1,2-dihydroquinoline", Col. 4514E & Izv. Vysshikh Uchebn. Zavedenii, Khim. I Khim. Tekhnol., vol. 5, No. 2, 1962, pp. 277–279.
Kautschuk Und Gummi—Kunststoffe—Asbest., vol. 42, No. 6, 1989, Heidelberg De, pp. 502–505, I. Pokluda et al., "Degradation of Polyester Fibres in Vulcanized Rubber and Loss of their Strength during Vulcanization".
CA #78:31137 (1972).*
CA #92:77796 (1979).*
CA Registry #26780–96–1 (not dated).*
*In Re Malzollhi*, 439 E.2d 220, 169 USPQ 367 (CCPA 1971) [Full Text].*
Derwent Abstract (World Patent Index) 26077 A/14 (1978).
Derwent Abstract (World Patent Index) 18747 E/10 (1982).
Derwent Abstract (World Patent Index) 55932 E/27 (1982).
Derwent Abstract (World Patent Index) 86–084983/13 (1986).
Derwent Abstract (World Patent Index) 91–020682/03 (1990).

* cited by examiner

*Primary Examiner*—Jeffrey E. Russel
(74) *Attorney, Agent, or Firm*—Stevens, Davis, Miller & Mosher

(57) ABSTRACT

A base rubber selected from natural rubber and diene rubber is blended with, based on 100 parts by weight of the base rubber, 0.5 to 5 parts by weight of a 2,2,4-trimethyl-1,2-dihydroquinoline polymer having a primary amine content of not more than 1% by weight, a monomer content of not more than 3% by weight and a dimer content of at least 30% by weight. The resulting rubber composition is vulcanized in contact with a reinforcing material such as an organic fiber or a steel cord. The rubber article thus obtained and reinforced with the reinforcing material is excellent in adhesiveness between the rubber and the reinforcing material, and further in thermal resistance.

4 Claims, No Drawings

REINFORCED RUBBER ARTICLE, PRODUCTION THEREOF AND RUBBER COMPOSITION SUITABLE THEREFOR

This is a division of application Ser. No. 08/193,758, filed Feb. 3, 1994, now Abandoned.

The present invention relates to a rubber article which is reinforced with a reinforcing material such as an organic fiber cord or a steel cord and can be used for automobile tires, conveyor belts, hoses and the like. The invention also relates to the production of the rubber article and further to a rubber composition suitable for coating an organic fiber cord as well as to another rubber composition suitable for coating a steel cord.

Organic fiber cords such as polyester, polyamide and aramid, or steel cords, particularly plated steel cords, such as brass-plated ones and zinc-plated ones are generally and widely used as a reinforcing material for rubber articles including automobile tires, conveyor belts, hoses and the like in order to improve and maintain strength and durability characteristics of the articles.

Of the organic fiber cords, polyester fibers are excellent in thermal resistance and fatigue resistance as well as in dimensional stability, and rubber tires formed by using the polyester fibers have such characteristics as large transverse stiffness and good steering stability. Thus, the polyester fibers are widely used in many rubber articles including rubber tires for automobiles.

Nevertheless, the polyester fibers have a problem in that the adhesion thereof to a coating rubber composition is poor. Accordingly there have been adopted some measures including a method of pretreating the polyester fibers with an adhesive such as resorcin or a resorcinolic resin, a method of incorporating such an adhesive into rubber during processing, and others. Although the use of the adhesive increases initial adhesiveness between the rubber and the polyester fibers, it causes the polyester cord itself to be thermally degraded, and further causes the rubber to be poor in thermal resistance and flex cracking resistance.

Besides, in order to improve the adhesiveness between a steel cord and coating rubber comprising natural rubber or synthetic rubber, there has hitherto been known a method of incorporating sulfur and an organic acid cobalt salt such as cobalt naphthenate into the rubber. Although the use of such a rubber composition for coating the steel cord increases the initial adhesiveness between the rubber and the steel cord, it deteriorates thermal resistance and flex cracking resistance of the rubber due to the incorporation of the organic acid cobalt salt.

On the other hand, there is known a method for improving the thermal resistance and flex cracking resistance of the rubber by incorporating any of various amine type antidegradants. The amine type antidegradants known for that purpose include, for example, N-isopropyl-N'-phenyl-p-diaminobenzene, N-(1,3-dimethylbutyl)-N'-phenyl-p-diaminobenzene, N,N'-diphenyl-p-diaminobenzene, N,N'-ditolyl-p-diaminobenzene, a condensation product of acetone and diphenylamine, a 2,2,4-trimethyl-1,2-dihydroquinoline polymer, and the like.

However, when rubber is blended with such a conventional antidegradant and subjected to adhesion to organic fibers, the resulting rubber articles have some problems in that they are insufficient in antidegradation properties such as thermal resistance, and also in that the incorporation of the antidegradant adversely affects the adhesion properties to cause insufficiency in initial adhesiveness between the rubber and the organic fibers and cause deterioration of adhesiveness after thermal aging. Due to such problems, the antidegradants are much restricted in their kinds and loading amounts, and hence it is not able to fully satisfy both the requirements, i.e. the adhesion properties of the rubber to the polyester cord and the thermal resistance of the rubber.

When rubber is blended with the conventional antidegradant and subjected to adhesion to a steel cord, the resulting rubber articles have some problems in that they are insufficient in antidegradation properties such as thermal resistance and flex cracking resistance, and also in that the incorporation of the antidegradant adversely affects adhesiveness between the rubber and the steel cord, especially adhesion properties after thermal aging in the moist state.

Under such circumstances, the present inventors have made intensive research to solve the defects in the conventionally known antidegradants, and resultantly have found that blending a certain base rubber with a specific amount of a 2,2,4-trimethyl-1,2-dihydroquinoline polymer having particular formation improves adhesiveness between the rubber and a reinforcing material and further improves the thermal resistance of the rubber, thereby accomplishing the present invention.

Thus the invention provides a reinforced rubber article which comprises a rubber composition comprising 100 parts by weight of a base rubber selected from natural rubber and diene rubber, and 0.5 to 5 parts by weight of a 2,2,4-trimethyl-1,2-dihydroquinoline polymer having a primary amine content of not more than 1% by weight, a monomer content of not more than 3% by weight and a dimer content of at least 30% by weight; and a reinforcing material present in contact with the rubber composition; wherein the rubber composition is vulcanized in contact with the reinforcing material.

The invention also provides a method for producing a reinforced rubber article by blending 100 parts by weight of a base rubber selected from natural rubber and diene rubber with 0.5 to 5 parts by weight of a 2,2,4-trimethyl-1,2-dihydroquinoline polymer having a primary amine content of not more than 1% by weight, a monomer content of not more than 3% by weight and a dimer content of at least 30% by weight, and vulcanizing the resulting rubber composition in contact with a reinforcing material.

Incorporation of such a 2,2,4-trimethyl-1,2-dihydroquinoline polymer having particular formation into the rubber in a specific amount improves the adhesiveness of the rubber not only to polyester fibers but also to other organic fibers such as polyamide fibers and aramid fibers, and resultantly produces rubber articles having excellent thermal resistance with holding high adhesion properties between the rubber and the organic fibers.

When the 2,2,4-trimethyl-1,2-dihydroquinoline polymer is applied to a system for adhering rubber to an organic fiber cord, it is preferred to treat the organic fiber cord with a resorcinolic adhesive before embedding the cord into rubber or to additionally incorporate a resorcinolic adhesive into the rubber.

Thus the invention further provides a rubber composition comprising a base rubber selected from natural rubber and diene rubber and, based on 100 parts by weight of the base rubber, 0.5 to 8 parts by weight of a resorcinolic adhesive, and 0.5 to 5 parts by weight of a 2,2,4-trimethyl-1,2-dihydroquinoline polymer having a primary amine content of not more than 1% by weight, a monomer content of not more than 3% by weight and a dimer content of at least 30% by weight.

When the 2,2,4-trimethyl-1,2-dihydroquinoline polymer is applied to a system for adhering rubber to a steel cord, it is preferred to additionally use an organic acid cobalt salt and sulfur in combination. Incorporation of the organic acid cobalt salt, the sulfur and the 2,2,4-trimethyl-1,2-dihydroquinoline polymer having particular formation into the rubber each in specific amounts achieves improvements in adhesion properties between the rubber and the steel cord, especially inhibits deterioration in adhesiveness after thermal aging in the moist state, and further improves thermal resistance and flex cracking resistance of the rubber.

Thus the invention still further provides a rubber composition comprising a base rubber selected from natural rubber and diene rubber and, based on 100 parts by weight of the base rubber, 0.1 to 1 part by weight, as cobalt, of an organic acid cobalt salt, 2 to 10 parts by weight of sulfur, and 0.5 to 5 parts by weight of a 2,2,4-trimethyl-1,2-dihydroquinoline polymer having a primary amine content of not more than 1% by weight, a monomer content of not more than 3% by weight and a dimer content of at least 30% by weight.

This rubber composition is especially effective for adhering to a steel cord with vulcanization, since it produces a rubber article reinforced with the steel cord and having excellent thermal resistance and flex cracking resistance with holding high adhesion properties between the rubber and the steel cord.

A first aspect of the present invention consists in making the primary amine content of the antidegradant 1% by weight or less, from the viewpoint that the antidegradant does not adversely affect the adhesion properties between rubber and a reinforcing material. It has been found that the primary amine components in the antidegradant decrease initial adhesiveness between the rubber and the reinforcing material, and further that, as a more considerable problem, they significantly decrease adhesiveness after thermal aging. It has also been found that the primary amine components easily bloom on the surface of unvulcanized rubber, thereby causing a further decrease of the adhesiveness between the rubber and the reinforcing material. Thus according to the invention, the amount of the primary amine components in the antidegradant should be controlled to 1% by weight or less.

A second aspect of the present invention consists, from the viewpoint for increasing thermal resistance of rubber, in the use of the 2,2,4-trimethyl-1,2-dihydroquinoline polymer containing 30% by weight or more of a 2,2,4-trimethyl-1, 2-dihydroquinoline dimer, which exhibits superior antidegradation properties for a long period, and containing 3% by weight or less of a monomer, which has a low molecular weight and easily volatilizes. When rubber is blended with an antidegradant, it is necessary for the antidegradant to have high dispersibility into the rubber. Further considering durability of the thermal resistance properties for a long period during practical use of rubber articles, it is also necessary for the antidegradant to hardly fume away from the rubber even under thermally degradational conditions. Thus, antidegradants having a low molecular weight are unfavorable because of their volatility. From the above points of view, the 2,2,4-trimethyl-1,2-dihydroquinoline polymer having a small monomer content and a large dimer content is used as an antidegradant in a prescribed amount according to the invention. The smaller monomer content is preferred and, for example, a monomer content of 1% by weight or less is more preferred. The larger dimer content is also preferred and, for example, a dimer content of 35% by weight or more is more preferred.

2,2,4-trimethyl-1,2-dihydroquinoline polymers are usually produced by the reaction of aniline with acetone, diacetone alcohol or mesityl oxide in a heated state and in the presence of an acid catalyst. They mainly have, in general, a structure represented by the following formula (I):

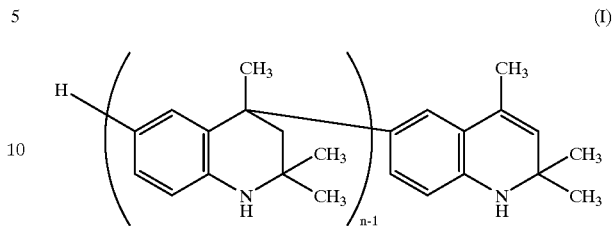

(I)

wherein n is an integer of 1 or more.

The monomer referred to in the invention is a compound of the formula (I) in which n is 1, the dimer is a compound of the formula (I) in which n is 2, followed by a trimer, a tetramer, . . . , corresponding to those of n=3, n=4, . . . , respectively. The primary amines are formed dominantly due to the starting aniline, and may have various structures. Representative examples thereof are those having structures of the following formulas:

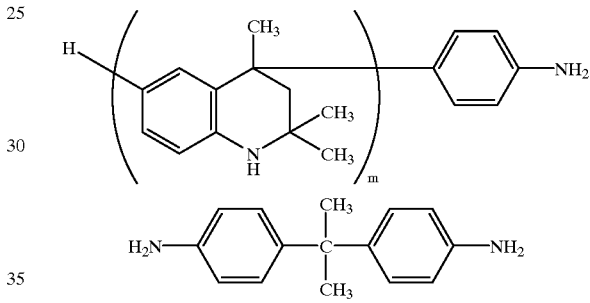

wherein m is an integer of 1 or more.

Since commercially available 2,2,4-trimethyl-1,2-dihydroquinoline polymers have various grades in quality, those for use in the invention should be chosen carefully. It is necessary in the invention to use a 2,2,4-trimethyl-1,2-dihydroquinoline polymer having a small primary amine content and a small monomer content as well as having a large dimer content, and the polymers meeting the requirements specified in the invention may be chosen from commercially available ones. However, the polymers are preferably produced in the following manner.

In the first place, aniline is subjected to a reaction with acetone, diacetone alcohol or mesityl oxide in a heated state and in the presence of an acid catalyst such as hydrochloric acid, hydrobromic acid, hydrofluoric acid, iodine, an organic sulfonic acid, boron trifluoride or a mixture of two or more thereof, and the resulting reaction product is purified by distillation to prepare a 2,2,4-trimethyl-1,2-dihydroquinoline monomer. It is preferred to make the monomer purity higher and higher, in general, 85% by weight or more, and it is more preferred to purify the monomer to a purity of 90% by weight or more.

The 2,2,4-trimethyl-1,2-dihydroquinoline monomer thus purified is then subjected to a reaction in a heated state and in the presence of an acid catalyst such as hydrochloric acid or others as described above to obtain a polymer mixture, from which the unreacted monomer is removed. In this reaction, for example, when a hydrochloric acid catalyst is applied, hydrochloric acid is used preferably with a concentration in the range of from about 15 to about 25% by weight and in an amount ranging from about 0.2 to about 0.5 time by mole based on the total amount of the starting 2,2,4-trimethyl-1,2-dihydroquinoline monomer and other amines contained therein as impurities. The reaction temperature is preferably from about 80° to about 100° C. Adopting such mild conditions can produce the polymer having a large dimer content. Removal of the unreacted monomer is, in general, carried out by distillation to distill off the low boiling volatiles.

According to the invention, the 2,2,4-trimethyl-1,2-dihydroquinoline polymer of particular formation as explained above is used. Particularly preferred is that the total amount of the dimer, trimer and tetramer, i.e. compounds of the above formula (I) in which n is 2, 3 and 4, is 75% by weight or more of the polymer, and more preferred is that the total amount of the dimer, trimer and tetramer is 80% by weight or more of the polymer.

Such a 2,2,4-trimethyl-1,2-dihydroquinoline polymer having small contents of primary amines and a monomer as well as having a large content of a dimer is incorporated into the base rubber according to the invention in an amount of 0.5 to 5 parts by weight per 100 parts by weight of the base rubber. Its amount smaller than 0.5 part by weight is insufficient for the thermal resistance of the rubber, and its amount larger than 5 parts by weight deteriorates the adhesion properties, both of which are unfavorable in the invention.

The base rubber to be used in the invention is natural rubber or diene rubber, which can be used each alone or as a rubber blend comprising two or more thereof. The diene rubber includes, for example, styrene-butadiene copolymer rubber, butadiene rubber, isoprene rubber, chloroprene rubber, ethylene-propylenediene copolymer rubber, and the like.

The rubber composition comprising the base rubber and the 2,2,4-trimethyl-1,2-dihydroquinoline polymer is usually further blended with a vulcanizing agent, preferably sulfur, since the composition is then vulcanized while keeping it in contact with a reinforcing material. The sulfur as a vulcanizing agent can be any of insoluble sulfur and various kinds of soluble sulfur which are ordinarily used in rubber industries, and is usually added in an amount ranging from about 0.5 to about 10 parts by weight per 100 parts by weight of the base rubber.

In order to reinforce the rubber composition containing the 2,2,4-trimethyl-1,2-dihydroquinoline polymer of particular formation, a reinforcing material is used. The reinforcing material can be any of organic fiber cords and steel cords which are commonly used in automobile tires, conveyor belts, hoses and the like.

In case of an organic fiber cord, preferred are polyester, polyamide, aramid and the like, and the present invention is especially effective for the polyester fibers. The organic fibers to be used are preferably pretreated with a resorcinolic adhesive. The resorcinolic adhesive referred to herein can be resorcin itself, and besides a resorcinolic resin including, for example, resorcin formaldehyde resins, resorcin alkylphenol formaldehyde resins, resorcin p-chlorophenol formaldehyde resins, mixtures of a resorcin formaldehyde resin and an alkylphenol formaldehyde resin, mixtures of a resorcin formaldehyde resin and a resorcin sulfide resin, or the like.

When the organic fibers treated with a resorcinolic adhesive are embedded in the rubber composition comprising the base rubber and the 2,2,4-trimethyl-1,2-dihydroquinoline polymer, a certain degree of adhesiveness can be achieved even though the rubber composition is blended with no further adhesives. In case of the organic fibers not treated with a resorcinolic adhesive or in case of desiring to ensure more sufficient adhesiveness, it is preferred to incorporate an adhesive into the rubber composition in the step of processing the rubber. The adhesive to be used herein is also resorcinolic one, which can be resorcin itself, and besides a resorcinolic resin including, for example, resorcin formaldehyde resins, resorcin alkylphenol formaldehyde resins, mixtures of a resorcin formaldehyde resin and an alkylphenol formaldehyde resin, and the like. When the resorcinolic adhesive is used, it is incorporated usually in an amount of 8 parts by weight or less, preferably about 0.5 to 8 parts by weight, and more preferably about 0.5 to about 5 parts by weight, per 100 parts by weight of the base rubber.

In order to more ensure the adhesiveness between the rubber and the organic fiber cord, it is also effective to incorporate a formaldehyde donor, i.e. a compound which releases formaldehyde upon heating, together with the resorninolic adhesive. The formaldehyde donor referred to herein can be any one which is conventionally used together with formaldehyde acceptors such as resorcin or resorcinolic resins, and it includes, for example, a condensation product of melamine and formaldehyde, such as dimethylolmelamine, trimethylolmelamine, tetramethylolmelamine and hexamethylolmelamine, a condensation product of melamine, formaldehyde and methanol, such as hexakis(methoxymethyl)melamine and pentakis(methoxymethyl)methylolmelamine, hexamethylenetetramine and the like. When the formaldehyde donor is used, it is incorporated, in general, in an amount of 8 parts by weight or less, preferably 0.5 to 8 parts by weight, and more preferably about 0.5 to about 5 parts by weight, per 100 parts by weight of the base rubber.

When the organic fiber cord is applied, the rubber composition for coating the cord preferably contains sulfur as a vulcanizing agent in an amount ranging from about 0.5 to about 8 parts by weight per 100 parts by weight of the base rubber.

In case of a steel cord, it includes, for example, a brass-plated steel cord, a zinc-plated steel cord, and the like. When the base rubber containing the 2,2,4-trimethyl-1,2-dihydroquinoline polymer is reinforced with the steel cord, the base rubber preferably further contains an organic acid cobalt salt and sulfur.

The organic acid cobalt salt to be incorporated into the base rubber can be any one which is conventionally used in the rubber for coating the steel cord, and includes, for example, cobalt naphthenate, cobalt caprylate, cobalt laurate, cobalt tridecanoate, cobalt palmitate, cobalt stearate, cobalt oleate, cobalt alaninate or the like. The amount of an organic acid cobalt salt to be incorporated is preferably in the range of from 0.1 to 1 part by weight, as a quantity of cobalt, per 100 parts by weight of the base rubber. The amount of cobalt smaller than 0.1 part by weight is hardly effective for the sufficient adhesion to the steel cord, while the amount of cobalt larger than 1 part by weight causes the resulting rubber article to have decreased thermal resistance and flex cracking resistance, and is unfavorable.

The sulfur to be incorporated here can be any one which is ordinarily used in rubber industries. Insoluble sulfur can be used in many cases, but other various kinds of soluble sulfur or mixtures of two or more kinds of sulfur may also be used. The amount of sulfur to be incorporated is preferably in the range of from 2 to 10 parts by weight per 100 parts by weight of the base rubber. The amount of sulfur smaller than 2 parts by weight is insufficient for the adhesion to the steel cord, and further unfavorable for the toughness and strength of the rubber article. The amount of sulfur larger than 10 parts by weight causes the resulting rubber article to have decreased thermal resistance and flex cracking resistance, and is unfavorable.

The resorcinolic adhesive as explained above may be used also in case of reinforcing the rubber composition with a steel cord. Further the formaldehyde donor as explained above may be used together with the resorcinolic adhesive also in case of reinforcing the rubber composition with the steel cord.

According to the invention, any of various fillers, for example, inorganic fillers such as carbon black, silica, clay, calcium carbonate and glass fibers, which are ordinarily used in rubber industries, can be incorporated into the base rubber, if occasion demands. Of these, carbon black is preferably used. The carbon black to be incorporated can be any one ordinarily used in rubber industries, and includes, for example, SAF, ISAF, HAF, FEF, SRF, GPF, MT, and the like. The loading amount of the filler is not particularly limited, but is preferably in the range of from about 20 to about 150 parts by weight per 100 parts by weight of the base rubber from the viewpoints of reinforcement and strength of the rubber. Furthermore, separately from the carbon black or in addition to the carbon black, it is preferred to incorporate hydrated silica for the purpose of increasing adhesiveness, and its loading amount is preferably in the range of from 5 to 80 parts by weight per 100 parts by weight of the base rubber.

It is also possible in the invention to additionally incorporate any other rubber chemicals conventionally used in the art, if occasion demands. Such rubber chemicals include, for example, other antioxidants, cross linking agents, vulcanization accelerators, retarders, peptizers, softeners, petroleum resins, lubricants, plasticizers, tackifiers, and the like.

The rubber composition thus compounded is vulcanized in contact with a reinforcing material such as an organic fiber cord or a steel cord, as described above. There is no particular limitation in vulcanizing conditions, and the vulcanization may be carried out under the conditions ordinarily and conventionally applied in the art. The vulcanizing conditions widely vary depending upon compositions of rubber to be used or upon desired articles, but those suited for the compositions of rubber or the desired articles can be selected, in general, from temperatures ranging from about 100° to about 200° C. and periods ranging from about 1 minute to about 2 hours. Thus, the rubber composition is molded in contact with a reinforcing material and vulcanized in a conventionally applied manner. The rubber articles thus manufactured and reinforced with an organic fiber cord or a steel cord exhibit excellent adhesiveness and thermal resistance.

The rubber articles according to the invention can be applied to automobile tires and other industrial parts. For example, those reinforced with organic fiber cords can be used as carcasses and the like in the tires, while those reinforced with steel cords can be used as belts (positioned between a tread and a carcass), carcasses, beads and the like in the tires.

A rubber composition containing a 2,2,4-trimethyl-1,2-dihydroquinoline polymer of particular formation and a resorcinolic adhesive as specified above is effective for use in reinforcement with an organic fiber cord.

Another rubber composition containing a 2,2,4-trimethyl-1,2-dihydroquinoline polymer of particular formation, sulfur and an organic acid cobalt salt as specified above is effective for use in reinforcement with a steel cord, and exhibits excellent adhesiveness, thermal resistance and flex cracking resistance when applied to various parts of automobile tires or other rubber articles. This rubber composition is, for example, applied to tires, especially belts, carcasses or beads thereof, molded and vulcanized in contact with a steel cord in a usual manner adopted in tire industries to manufacture tires.

Next, the present invention is explained in more detail with reference to the following examples, which are only illustrative but not limitative to the scope of the invention. In the examples, percentage and parts indicating loading amounts or contents are % by weight and parts by weight, respectively, unless otherwise specified.

REFERENCE EXAMPLE 1

In a 500 ml, four-necked flask equipped with an acetone-introducing means, a thermometer, a stirrer and a condenser were placed 121 g (1.3 moles) of aniline and 12.4 g of p-toluenesulfonic acid monohydrate (0.065 mole as p-toluenesulfonic acid), and they were heated. While the inner temperature was kept at 95–100° C., 755 g of acetone was introduced into the flask over the course of eight hours. The reaction mixture was diluted with 100 ml of toluene and neutralized with 2.6 g of sodium hydroxide and 50 ml of water while the temperature was kept at 85–95° C., and then, the mixture was allowed to stand to be separated into two layers, after which the aqueous layer formed was removed. The oil layer obtained was washed with several 100 ml portions of water. When the mixture of the oil layer and water became neutral, the toluene layer was separated and toluene was removed therefrom by distillation, after which the residue was rectified under reduced pressure to obtain 20 g of an unreacted aniline fraction up to a boiling point of 100° C./10 mmHg and 142.4 g of a monomer fraction between a boiling point of 100° C./10 mmHg and a boiling point of 90° C./2 mmHg.

This monomer fraction was analyzed by gas chromatography to find that the composition ratio was as follows:

| | |
|---|---|
| 2,2,4-Trimethyl-1,2-dihydroquinoline | 97.0% |
| Aniline | 0.2% |
| Low-boiling impurities | 2.8% |

Subsequently, in a 500 ml, four-necked flask equipped with a thermometer, a stirrer and a condenser were placed 100 g of the monomer fraction obtained above, 20.9 g of conc. hydrochloric acid and 20 ml of water, and the resulting mixture was heated to 90° C., and further stirred for six hours while the temperature was kept at 90–100° C. Thereafter, the reaction mixture was diluted with 100 ml of toluene, and 19.8 g of a 45% aqueous sodium hydroxide solution was added thereto while the temperature was kept at 85–90° C. to neutralize the reaction mixture, after which the mixture was allowed to stand to be separated into two layers. The aqueous layer formed was removed, and the toluene layer obtained was washed with several 100 ml portions of water.

The toluene layer was separated and toluene was removed therefrom by distillation, after which the residue was further distilled at an inner temperature of 200° C. until the pressure was reduced to 2 mmHg to remove 21.8 g of a low-boiling fraction, thereby obtaining 73.2 g of a 2,2,4-trimethyl-1,2-dihydroquinoline polymer as the residue. This polymer is referred to hereinafter as Antidegradant A. Antidegradant A was subjected to quantitative analysis to find that the components were as shown in Table 1.

The quantitative analysis of a monomer, a dimer, a trimer and a tetramer was conducted by gas chromatography using dibutyl phthalate as an internal standard and under the following conditions:

Column: A 3 mmφ×0.5 m separating tube manufactured by G.L. Science and packed with a Chromosorb W AW carrier coated with a 3% silicon OV-1 liquid layer Injection temperature: 350° C.

Column temperature: Elevated at a rate of 10° C./min from 100° C. to 350° C.

Carrier gas: Nitrogen (50 ml/min)

Detector: Flame ionization detector

The primary amine content was determined by dissolving the polymer in chloroform, adding hydrochloric acid and p-dimethylaminobenzaldehyde thereto to prepare a sample solution, measuring the absorbance of the sample solution by a spectrophotometer at a wavelength of 440 nm, subtracting a blank test value from the absorbance obtained and applying the value obtained to a calibration curve.

REFERENCE EXAMPLE 2

In a 500 ml, four-necked flask equipped with an acetone-introducing means, a thermometer, a stirrer and a water-separator which was connected to a reflux condenser at its top were placed 93.1 g (1 mole) of aniline, 27 g (0.27 mole) of conc. hydrochloric acid and 3 g of n-hexane, and the resulting mixture was heated. n-Hexane had previously been placed in the water-separator. When the inner temperature of the flask reached 85° C., the introduction of acetone was started and 174 g (3 moles) of acetone was introduced into the flask over the course of eight hours while the temperature was kept at 70–90° C. The water produced by condensation reaction was removed together with n-hexane by azeotropic distillation from the flask. In the water-separator, n-hexane and water separated into the upper layer and the lower layer, respectively, and hence, were separately and continuously taken out of the system. After completion of the introduction of acetone, the reaction mixture was neutralized with 15 g of a 28% aqueous sodium hydroxide solution and 100 ml of water while the temperature was kept at 60–80° C., then diluted with 100 ml of toluene and thereafter filtered through a G3 glass filter coated with a filter aid to remove the catalyst residue. The filtrate was allowed to stand to be separated into two layers, and the aqueous layer formed was removed.

The oil layer obtained was washed with several 100 ml portions of water and when the mixture of the oil layer and water became neutral, the oil layer was separated, thereafter distilled to remove low-boiling fractions such as n-hexane, toluene and unreacted acetone, and then further rectified under reduced pressure to obtain 23 g of an unreacted aniline fraction until a boiling point of 100° C./10 mmHg and remove 57.5 g of a 2,2,4-trimethyl-1,2-dihydroquinoline monomer fraction (purity of 96.8% as measured by gas chromatography) between a boiling point of 100° C./10 mmHg and a boiling point of 90° C./2 mmHg, thereby obtaining 82.6 g of a 2,2,4-trimethyl-1,2-dihydroquinoline polymer as the residue. This polymer is referred to hereinafter as Antidegradant X. Antidegradant X was subjected to quantitative analysis in the same manner as in Reference Example 1 to find that the components were as shown in Table 1.

REFERENCE EXAMPLE 3

The same procedure as in Reference Example 1 was repeated, except that 100 g of a monomer fraction obtained in the same manner as in Reference Example 1 was placed together with 60.8 g (0.6 mole) of conc. hydrochloric acid and 30 ml of water in the flask, and finally 14.5 g of the low-boiling fraction was removed to obtain 80.5 g of a 2,2,4-trimethyl-1,2-dihydroquinoline polymer as the residue. This polymer is referred to hereinafter as Antidegradant Y. Antidegradant Y was subjected to quantitative analysis in the same manner as in Reference Example 1 to find that the components were as shown in Table 1.

REFERENCE EXAMPLE 4

The same procedure as in Reference Example 1 was repeated, but an unreacted aniline fraction in the rectification after the monomer condensation was collected up to a boiling point of 100° C./20 mmHg to obtain 14 g of the fraction, and thereafter a monomer fraction was obtained between a boiling point of 100° C./20 mmHg and a boiling point of 90° C./2 mmHg in an amount of 148.6 g with a monomer purity of 84.2% and an aniline content of 4.8%. After that, the same polymerization and after-treatment as in Reference Example 1 were conducted to obtain 71.6 g of a 2,2,4-trimethyl-1,2-dihydroquinoline polymer as the residue. The polymer is referred to hereinafter as Antidegradant Z. Antidegradant Z was subjected to quantitative analysis in the same manner as in Reference Example 1 to find that the components were as shown in Table 1.

TABLE 1

| | Antidegradant | | | |
|---|---|---|---|---|
| Component | A | X | Y | Z |
| Monomer (%) | 0.3 | 4.9 | 0.6 | 0.2 |
| Dimer (%) | 40.4 | 17.8 | 23.4 | 39.9 |
| Trimer (%) | 29.5 | 10.6 | 18.6 | 28.5 |
| Tetramer (%) | 15.4 | 7.2 | 11.2 | 15.1 |
| Primary amine (%) | 0.43 | 2.3 | 0.70 | 1.70 |
| Remarks | Present invention | Comparison | | |

In addition to these Antidegradants A, X, Y and Z, N-(1,3-dimethylbutyl)-N'-phenyl-p-diaminobenzene (referred to hereinafter as Antidegradant V) was also used in the following Examples.

EXAMPLE 1

TABLE 2

| Compounding recipe | |
|---|---|
| Natural rubber (RSS#1) | 70 parts |
| Butadiene rubber (BR-01 manufactured by Japan Synthetic Rubber Co., Ltd.) | 15 parts |
| Styrene-butadiene copolymer rubber (#1500) | 15 parts |
| HAF carbon black (N330) | 45 parts |
| Stearic acid | 2 parts |
| Aromatic oil | 12 parts |
| Zinc oxide | 3 parts |
| Antidegradant | Shown in Table 3 |
| Resorcin formaldehyde resin | 1.5 parts |
| Vulcanization accelerator (N-cyclohexyl-2-benzo-thiazolesulfenamide) | 1.1 parts |
| Sulfur | 3 parts |
| Methoxylated methylolmelamine resin (Sumikanol 507 manufactured by Sumitomo Chemical Co., Ltd.) | 4 parts |

Using a 600 ml Laboplastomill manufactured by Toyo Seiki as a Banbury mixer, a blend of the above three kinds of rubber was kneaded together with the carbon black, stearic acid, aromatic oil, zinc oxide, resorcin formaldehyde resin and antidegradant shown in the compounding recipe of Table 2 at an oil bath temperature of 150° C. and at a mixer revolution rate of 50 rpm for 15 minutes. The rubber temperature at this time was 160–170° C. Subsequently, this compound was transferred to an open mill, into which the vulcanization accelerator, sulfur and methoxylated methylolmelamine resin shown in the above compounding recipe were added and kneaded with the compound at a temperature of 50–70° C.

A part of the sample immediately after the kneading was vulcanized at 145° C. for 40 minutes to prepare thermal aging test specimens. Further, immediately after the preparation of the unvulcanized rubber compound, polyester fibers were embedded in the compound and immediately vulcanized by a vulcanization press at 145° C. for 40 minutes to prepare adhesion test specimens. The remaining compound was allowed to stand at room temperature for three days, and thereafter, polyester fibers were embedded therein. The resulting assembly was vulcanized under the same conditions as above to prepare adhesion test specimens. The polyester fibers used in this Example were of 1100 d/3 and had been latex-treated with a resorcin p-chlorophenol formaldehyde resin.

Each of the test specimens thus obtained was subjected to tests for rubber properties in the following manner to obtain the results shown in Table 3 in which the varying amounts in the compounding recipe were also shown.

Initial Adhesiveness

The adhesion test specimens vulcanized and adhered to the polyester fibers immediately after the preparation of the unvulcanized rubber compound and the other adhesion test specimens vulcanized and adhered to the polyester fibers after allowing the unvulcanized rubber compound to stand at room temperature for three days were evaluated for adhesiveness by the H test method described in ASTM D 2138. Each of the test results is expressed by the average value of 12 specimens.

Adhesiveness After Thermal Aging

The adhesion test specimens vulcanized and adhered to the polyester fibers immediately after the preparation of the unvulcanized rubber compound were thermally aged at 100° C. for 72 hours and thereafter subjected to measurement of adhesion by the H test method described in ASTM D 2138. Each of the test results is expressed by the average value of 12 test specimens.

Adhesiveness After Thermal Aging in the Moist State

The adhesion test specimens vulcanized and adhered to the polyester fibers immediately after the preparation of the unvulcanized rubber compound were thermally aged in the moist state at a temperature of 50° C. and at a relative humidity of 80% for seven days, and thereafter, subjected to measurement of adhesion by the H test method described in ASTM D 2138. Each of the test results is expressed by the average value of 12 specimens.

Thermal Resistance

According to JIS K 6301, a dumbbell No. 3 test specimen was subjected to measurement of tensile strength before and after aging at 100° C. for 72 hours, and the tensile strength retention was calculated from the values obtained.

TABLE 3

| | Antidegradant | | Initial adhesiveness (kg) | |
|---|---|---|---|---|
| | Kind | Amount (parts) | Immediately vulcanized | Vulcanized after allowing to stand for three days |
| Present invention | A | 2 | 20.4 | 20.4 |
| Comparison | — | — | 20.5 | 20.6 |
| | X | 2 | 17.4 | 16.4 |
| | Y | 2 | 19.6 | 18.2 |
| | Z | 2 | 18.9 | 16.7 |
| | V | 2 | 18.5 | 17.3 |

| | Adhesiveness after thermal aging (kg) | Adhesiveness after thermal aging in the moist state (kg) | Thermal resistance Tensile strength retention (%) |
|---|---|---|---|
| Present invention | 15.0 | 15.5 | 36.6 |
| Comparison | 10.4 | 11.0 | 15.5 |
| | 13.0 | 13.3 | 26.3 |
| | 14.6 | 15.2 | 29.1 |
| | 12.4 | 13.8 | 35.1 |
| | 10.3 | 10.7 | 32.5 |

TABLE 4

| Compounding recipe | |
|---|---|
| Natural rubber (RSS#1) | 100 parts |
| HAF carbon black (N330) | 45 parts |
| Stearic acid | 3 parts |
| Hydrated silica (Nipsil VN3 manufactured by Nippon Silica Kogyo) | 10 parts |
| Zinc oxide | 2 parts |
| Antidegradant | Shown in Table 5 |
| Resorcin alkylphenol formaldehyde resin (Sumikanol 620 manufactured by Sumitomo Chemical Co., Ltd.) | 2 parts |
| Vulcanization accelerator (N-t-butyl-2-benzothiazolesulfenamide) | 1 part |
| Sulfur | 4 parts |
| Methoxylated methylolmelamine resin (Sumikanol 507 manufactured by Sumitomo Chemical Co., Ltd.) | 4 parts |

The natural rubber, carbon black, stearic acid, hydrated silica, zinc oxide, resorcin alkylphenol formaldehyde resin and antidegradant shown in the compounding recipe of Table 4 were placed at an oil bath temperature of 150° C. in a 600 ml Laboplastomill as a Banbury mixer manufactured by Toyo Seiki and kneaded at a mixer revolution rate of 50 rpm for 15 minutes. At this time, the rubber temperature was 160–170° C. Subsequently, the resulting compound was transferred to an open mill, into which the vulcanization accelerator, sulfur and methoxylated methylolmelamine resin shown in the compounding recipe of Table 4 were added and kneaded with the compound at a temperature of 50–70° C.

A part of the sample immediately after the kneading was vulcanized at 145° C. for 40 minutes to prepare thermal aging test specimens. Further, polyamide fibers were embedded in another part of the unvulcanized compound sample immediately after the preparation and, immediately thereafter, the resulting assembly was vulcanized by a vulcanization press at 145° C. for 40 minutes to prepare adhesion test specimens. The remaining sample was allowed to stand at room temperature for three days, after which polyamide fibers were embedded therein, and the resulting assembly was vulcanized under the same conditions as above to prepare adhesion test specimens. The polyamide fibers used in this Example were of 1260 d/3 and had been latex-treated with a resorcin formaldehyde resin.

Each of the test specimens thus obtained was subjected to the tests for rubber properties in the same manner as in Example 1 to obtain the results shown in and Table 5 in which the varying amounts in the compounding recipe were also shown.

TABLE 5

| | Antidegradant | | Initial adhesiveness (kg) | |
|---|---|---|---|---|
| | Kind | Amount (parts) | Immediately vulcanized | Vulcanized after allowing to stand for three days |
| Present invention | A | 2 | 17.9 | 17.8 |
| Comparison | — | — | 18.5 | 18.2 |
| | X | 2 | 14.1 | 12.3 |
| | Y | 2 | 16.2 | 15.9 |
| | Z | 2 | 14.5 | 12.6 |
| | V | 2 | 15.4 | 13.3 |

| | Adhesiveness after thermal aging (kg) | Adhesiveness after thermal aging in the moist state (kg) | Thermal resistance Tensile strength retention (%) |
|---|---|---|---|
| Present invention | 14.3 | 14.5 | 45.9 |
| Comparison | 6.9 | 10.6 | 18.7 |
| | 10.4 | 10.9 | 30.2 |
| | 13.0 | 13.2 | 35.1 |
| | 11.4 | 11.8 | 44.2 |
| | 11.7 | 12.1 | 35.6 |

TABLE 6

| Compounding recipe | |
|---|---|
| Natural rubber (RSS#1) | 100 parts |
| HAF carbon black (N330) | 45 parts |
| Stearic acid | 3 parts |
| Hydrated silica (Nipsil VN3 manufactured by Nippon Silica Kogyo) | 10 parts |
| Zinc oxide | 2 parts |
| Antidegradant | Shown in Table 7 |
| Cobalt naphthenate (cobalt content of 10%) | 2 parts |
| Vulcanization accelerator (N,N-dicyclohexyl-2-benzothiazolesulfenamide) | 1.2 parts |
| Sulfur | 4 parts |

A 600 ml Laboplastomill manufactured by Toyo Seiki was used as a Banbury mixer, and the natural rubber, carbon black, stearic acid, hydrated silica, zinc oxide and antidegradant shown in the compound recipe of Table 6 were placed therein at an oil bath temperature of 150° C. and kneaded at a mixer revolution rate of 50 rpm for 15 minutes. At this time, the rubber temperature was 160–170° C. Subsequently, the resulting compound was transferred to an open mill, and the vulcanization accelerator, sulfur and cobalt naphthenate shown in the compound recipe of Table 6 were added thereto and kneaded with the compound at a temperature of 50–70° C.

A part of the sample immediately after the kneading was vulcanized at 145° C. for 40 minutes to prepare test specimens for thermal aging test and flex cracking test. Further, immediately after the preparation of the unvulcanized rubber compound, a brass-plated steel cord was embedded therein, and the resulting assembly was vulcanized by a vulcanization press at 145° C. for 40 minutes to prepare adhesion test specimens. The remaining sample was allowed to stand at room temperature for three days, and a brass-plated steel cord was then embedded therein, after which the resulting assembly was vulcanized under the same conditions as above to prepare adhesion test specimens.

The test specimens thus obtained were subjected to tests for rubber properties in the following manner to obtain the results shown in Table 7 in which the varying amounts in the compounding recipe of Table 6 were also shown.

Adhesiveness

The adhesion test specimens vulcanized and adhered to the steel cord immediately after the preparation of the unvulcanized rubber compound and the other adhesion test specimens vulcanized and adhered to the steel cord after allowing the unvulcanized rubber compound to stand for three days were evaluated for adhesiveness by the H test method described in ASTM D 2138. The test specimens vulcanized and adhered to the steel cord immediately after the preparation of the unvulcanized rubber compound were, in addition to the measurement of adhesion before thermal aging in the moist state, also subjected to the measurement of adhesion after thermal aging in the moist state at a temperature of 50° C. and at a relative humidity of 90% for seven days. Each of the test results is expressed by the average value of 12 test specimens.

Thermal Resistance

According to JIS K 6301, a dumbbell No. 3 test specimen was subjected to measurement of tensile strength before and after thermal aging at 100° C. for 72 hours. The tensile strength retention was calculated from the two values obtained.

Flex Cracking Resistance

According to JIS K 6301, a test specimen having a hole of 2.0 mm in original length was subjected to a flex cracking test using a de Mattia machine, and the length of cracking after 10,000 times of flexing was measured by means of slide calipers.

TABLE 7

| | | | Adhesiveness (kg) | |
|---|---|---|---|---|
| | | | Immediately vulcanized | Vulcanized |
| | Antidegradant | | Before thermal aging in | After thermal aging in | after allowing to stand |
| | Kind | Amount (parts) | the moist state | the moist state | for three days |
| Present invention | A | 2 | 31.9 | 25.5 | 31.8 |
| Comparison | — | — | 32.1 | 22.2 | 31.9 |
| | X | 2 | 28.3 | 18.4 | 27.6 |
| | Y | 2 | 30.9 | 23.2 | 31.7 |
| | Z | 2 | 30.5 | 19.5 | 28.8 |
| | V | 2 | 30.7 | 20.4 | 27.3 |

TABLE 7-continued

|  | Thermal resistance Tensile strength retention (%) | Flex cracking resistance After 10,000 times of flexing (mm) |
|---|---|---|
| Present invention | 46.4 | 5.10 |
| Comparison | 19.4 | 15.85 |
|  | 34.1 | 11.66 |
|  | 37.9 | 9.41 |
|  | 45.7 | 5.48 |
|  | 36.4 | 5.07 |

A reinforced rubber article according to the invention is improved in adhesion properties between rubber and a reinforcing material such as an organic fiber cord or a steel cord, in particular, it exhibits high adhesiveness even after thermal aging or after moist and thermal aging, and also holds good adhesiveness even in case that unvulcanized rubber is allowed to stand for a long period and thereafter subjected to vulcanization for adhering to the reinforcing material. Further the rubber article is superior in various properties including thermal resistance and the like.

A rubber composition containing a 2,2,4-trimethyl-1,2-dihydroquinoline polymer of particular formation and a resorcinolic adhesive is effective for coating an organic fiber cord.

Another rubber composition containing a 2,2,4-trimethyl-1,2-dihydroquinoline polymer of particular formation, sulfur and an organic acid cobalt salt is effective for coating a steel cord. When the rubber composition is subjected to vulcanization for adhering to a steel cord, it improves adhesiveness between the rubber and the steel cord, exhibits little decrease in adhesiveness even after moist and thermal aging, and holds good adhesiveness even after it is allowed to stand as unvulcanized for a long period. Further the rubber composition is superior in various properties including thermal resistance, flex cracking resistance and the like.

While the invention has been described with respect to specific embodiments and examples, it is to be understood by the skilled person that the invention is not limited to the embodiments and examples given herein but these may be modified within the spirit and scope of the appended claims.

What is claimed is:

1. A method for producing a reinforced rubber article which comprises:
   blending 100 parts by weight of a base rubber selected from natural rubber and diene rubber with 0.5 to 5 parts by weight of a 2,2,4-trimethyl-1,2-dihydroquinoline polymer having a primary amine content of not more than 1% by weight, a monomer content of not OL more than 3% by weight and a dimer content of at least 30% by weight; and
   vulcanizing the resulting rubber composition in contact with a reinforcing material.

2. A method according to claim 1, wherein the reinforcing material is an organic fiber.

3. A method according to claim 1, wherein the reinforcing material is a steel cord.

4. A method according to claim 3, wherein the base rubber is further blended with 0.1 to 1 part by weight, as cobalt, of an organic acid cobalt salt, and 2 to 10 parts by weight of sulfur.

* * * * *